United States Patent [19]

Smethers et al.

[11] Patent Number: 5,310,523
[45] Date of Patent: May 10, 1994

[54] SELF-CONTAINED ASSAY ASSEMBLY AND APPARATUS

[75] Inventors: Rick T. Smethers, Milpitas; Lev J. Leytes, Palo Alto; Brian D. Warner, Martinez; Robert R. Shadel, San Francisco; Michael S. Urdea, Alamo, all of Calif.

[73] Assignee: Chiron Corporation, Emeryville, Calif.

[21] Appl. No.: 750,325

[22] Filed: Aug. 27, 1991

Related U.S. Application Data

[63] Continuation-in-part of Ser. No. 539,002, Jun. 15, 1990, abandoned.

[51] Int. Cl.⁵ .................. G01N 21/01; G01N 31/22
[52] U.S. Cl. ........................... 422/57; 422/58; 422/61; 422/72; 422/102; 435/6; 435/7.1; 435/291; 435/312; 436/518
[58] Field of Search .................. 435/299–301, 435/810, 6, 287, 312, 291, 7.1; 422/57, 58, 61, 72, 102; 436/809, 165, 518

[56] References Cited

U.S. PATENT DOCUMENTS

| | | |
|---|---|---|
| 4,225,558 | 9/1980 | Peterson et al. |
| 4,274,885 | 6/1981 | Swartout |
| 4,390,499 | 6/1983 | Curtis |
| 4,469,793 | 9/1984 | Guigan |
| 4,519,981 | 5/1985 | Guigan |
| 4,654,127 | 3/1987 | Baker et al. |
| 4,769,333 | 9/1988 | Dole et al. |
| 4,806,316 | 2/1989 | Johnson et al. |
| 4,889,692 | 12/1989 | Holtzman |
| 4,978,502 | 12/1990 | Dole et al. |
| 5,124,246 | 6/1992 | Urdea et al. ............... 435/6 |

FOREIGN PATENT DOCUMENTS

| | | |
|---|---|---|
| 0318255A3 | 11/1988 | European Pat. Off. |
| 0369836A1 | 10/1989 | European Pat. Off. |
| 2609334 | 12/1987 | France |
| WO84/02004 | 5/1984 | PCT Int'l Appl. |

Primary Examiner—James C. Housel
Assistant Examiner—Jan M. Ludlow
Attorney, Agent, or Firm—Peter J. Dehlinger

[57] ABSTRACT

A self-contained assembly for assaying an analyte in a liquid sample. The pair of disc-like rotatable plates forming the assembly are relatively rotatable to align reagent reservoirs in one plate with a reaction well in the other plate, for sequential addition of multiple reagents, either in liquid or solid form, to the reaction well. In one embodiment, the reaction well includes solid-phase particles which can be transferred from the reaction well to spaced wells in the assembly by a combination of relative movement of the plate, and rotation of the entire assembly.

13 Claims, 10 Drawing Sheets

SELF-CONTAINED ASSAY ASSEMBLY AND APPARATUS

This application is a continuation-in-part of U.S. application Ser. No. 539,002, filed Jun. 15, 1990, now abandoned.

1. FIELD OF THE INVENTION

The present invention relates to an assembly for assaying an analyte in a liquid sample, and in particular, to a self-contained assembly which provides prepacked reagents which can be added to the sample in a defined sequence.

2. BACKGROUND OF THE INVENTION

Many analyte assays involve a sequence of reaction steps in which an analyte is reacted sequentially with two or more, reagents. Typically in this type of assay, a reagent is added and the mixture is allowed to react for a preselected time before addition of the next reagent. Where the assay involves analyte binding to a solid support, the reaction chamber containing analyte bound to the support may be washed between reagent-addition steps.

Ideally, it is desired to carry out multiple-addition assays of this type in a simple self-contained device which can be adapted for automated or semi-automated operation in a clinical setting, or alternatively, may be reliably practiced in a home or doctor's office setting by simple assay procedures.

Heretofore, a variety of self-contained diagnostic devices which provide multiple, prepackaged reagents have been proposed. U.S. Pat. No. 4,806,316 describes a disposable diagnostic device in which a liquid sample is distributed to multiple reaction wells which may contain prepackaged reagents for reaction with the analyte. The device may be adapted for sequential-reaction assays by transferring each sample successively through two or more wells, where the different wells contain the desired prepackaged reagents.

U.S. Pat. No. 4,519,981 shows a rotary diagnostic device containing a series of side-by-side, radially overlapping reaction chambers, each of which may contain a prepackaged reagent. The cells are interconnected to allow sample fluid flow from through each chamber to a successive chamber by centrifugal motion alternately in opposite directions. That is, fluid sample is moved from a first chamber to a second, side-adjacent chamber by rotating the device in one direction, and after a selected reaction time, the sample fluid is moved from the second-chamber to a side-adjacent third chamber by rotary motion in the opposite direction.

Another multi-reagent rotary device is disclosed in U.S. Pat. No. 4,390,499. The device includes a series of compartments separated by rupturable seals. In operation, pneumatic and centrifugal forces are used to break the seals between compartments, for sequential mixing of the reagent material with the sample.

U.S. Pat. No. 4,469,793 discloses a rotary diagnostic device in which a sample fluid is deposited in a radially inner well, and distributed in a predetermined volume to each of a plurality of outer receptor cells under centrifugal forces applied by spinning the device in one direction to force the sample first into overflow wells, then in the opposite direction to dispense the predetermined volumes of sample into the outer cells. The compartments of the cells may be supplied with different liquids for use in simultaneous analyses. Also disclosed in this patent is a solid reactor bead which is designed to pick up successively, a quantity of the analyte being measured, then a quantity of a reagent containing a biological indicator.

The above-described assay devices all involve relatively complicated pressure and/or centrifugal force mechanism for releasing prepackaged reagents into a sample or for transferring the sample from one reagent chamber to another. For this reason, the devices may be relatively expensive in manufacture, and also may be unreliable in operation, due to variations in centripetal or pneumatic force applied to the device during operation, or variations in the force needed to rupture seals or advance the sample between chambers, and/or variable volume losses which occur as a liquid is transferred from chamber to chamber.

3. SUMMARY OF THE INVENTION

The invention includes, in one aspect, a self-contained assembly for detecting an analyte ligand by detectable, analyte-specific binding to a solid support. The assembly includes a reaction plate having a well containing the solid support, and a transfer plate containing first and second reagents contained in separate first and second reservoirs. The transfer plate is mounted on the reaction plate for movement thereon to a sample-addition position, at which sample can be added to the well, one reagent-transfer position at which one reservoir is aligned with the well, a wash position at which wash solution can be introduced into the well, and another reagent-transfer position at which the second reservoir is aligned with the well. The transfer and reaction plates are designed to prevent release of reagents from their corresponding reservoirs until the associated reservoir is aligned with the well.

In one embodiment, the reagent is in the form of a liquid solution, the reservoir containing the solution includes a channel formed in the plate, and the channel is sealed at its opening in the transfer plate. Preferably the channel and seal are formed by an elastomeric sleeve held in a channel within the transfer plate, and the confronting planes of the transfer and reaction plates are spaced, adjacent the region of the sleeve, to form a capillary lock, to prevent liquid from leaking from the reservoir by capillarity. Also in a preferred embodiment, the transfer plate includes a chamfered opening communicating a reservoir in the transfer plate with the well in the reaction plate.

In another general embodiment, at least one of the reagents includes a pelletized form of the reagent, and the pelletized reagent is delivered from the associated reagent reservoir to the well by gravity, when the reagent reservoir is aligned with the reaction well.

The reaction well in the reaction plate may be formed by an elongate channel containing a solid-phase assay support. In this embodiment, the transfer plate may include ports which are alignable with spaced areas in the channel, when the transfer plate is moved to a wash position, forming an enclosed passageway for passing a solution through the channel.

In one method, the assembly is used for detecting a nucleic acid with a known target sequence. Here the solid-phase support in the reaction is coated with immobilized nucleic acid fragments, and the assembly includes reagent reservoirs for sequential addition to the reaction channel of (1) a probe effective to hybridize with both the target sequence and the immobilized fragments, and (2) a reporter molecule effective to bind, directly or indirectly, to the probe.

In another method, the assembly is used in an immunoassay for detection of a ligand effective to bind immunospecifically to the solid support. Here the assembly includes reagent reservoirs for sequential addition to the reaction channel of (1) an antiligand reagent capable to binding immunospecifically with the ligand, when the ligand is bound to the support, and (2) a reagent capable of reacting with the antiligand reagent to produce a detectable signal on the solid support.

In another aspect, the invention includes apparatus for detecting an analyte ligand by detectable, ligand-specific binding to a solid support. The apparatus includes a self-contained assembly of the type described above, and a device for holding the reaction plate, and rotating said transfer plate to its various positions.

In one embodiment, the device is effective to rotate the assembly as a unit, the reaction well includes a radially extending channel, the solid support surface includes at least two solid-phase particles carried in the channel for movement therein from inner toward outer radial positions, and the transfer plate includes a receiving slot into which the particles can be received, when the particles in the channel are subjected to an outward force, and the channel is aligned with said slot. The reaction plate includes particle-receiving wells into which particles in the slot can be deposited, when the reagent plate containing deposited particles is rotated with respect to the reaction plate.

In an embodiment of the device designed for heating the liquid contents of the well, the assembly further includes structure for sealing the well when heating is applied. The assembly includes a cover plate attached to the reaction plate, and the sealing structure includes (a) a sealing pad carried in the transfer plate floating in a direction normal to the plane of the plate, and (b) a cam surface in the cover plate for biasing the pad against the well platform, when the transfer plate is moved to a heating position.

Also in an embodiment of the device, the solid support includes a bead in the well, and the device includes a detector having a light sensor, and a tube extending from the light sensor and positionable to encompass a spherical surface portion of the bead.

These and objects and features of the invention will become more fully apparent when the following detailed description of the invention is read in conjunction with the accompanying drawings.

DETAILED DESCRIPTION OF THE INVENTION

A. Assay Assembly and Apparatus

Figure 1:
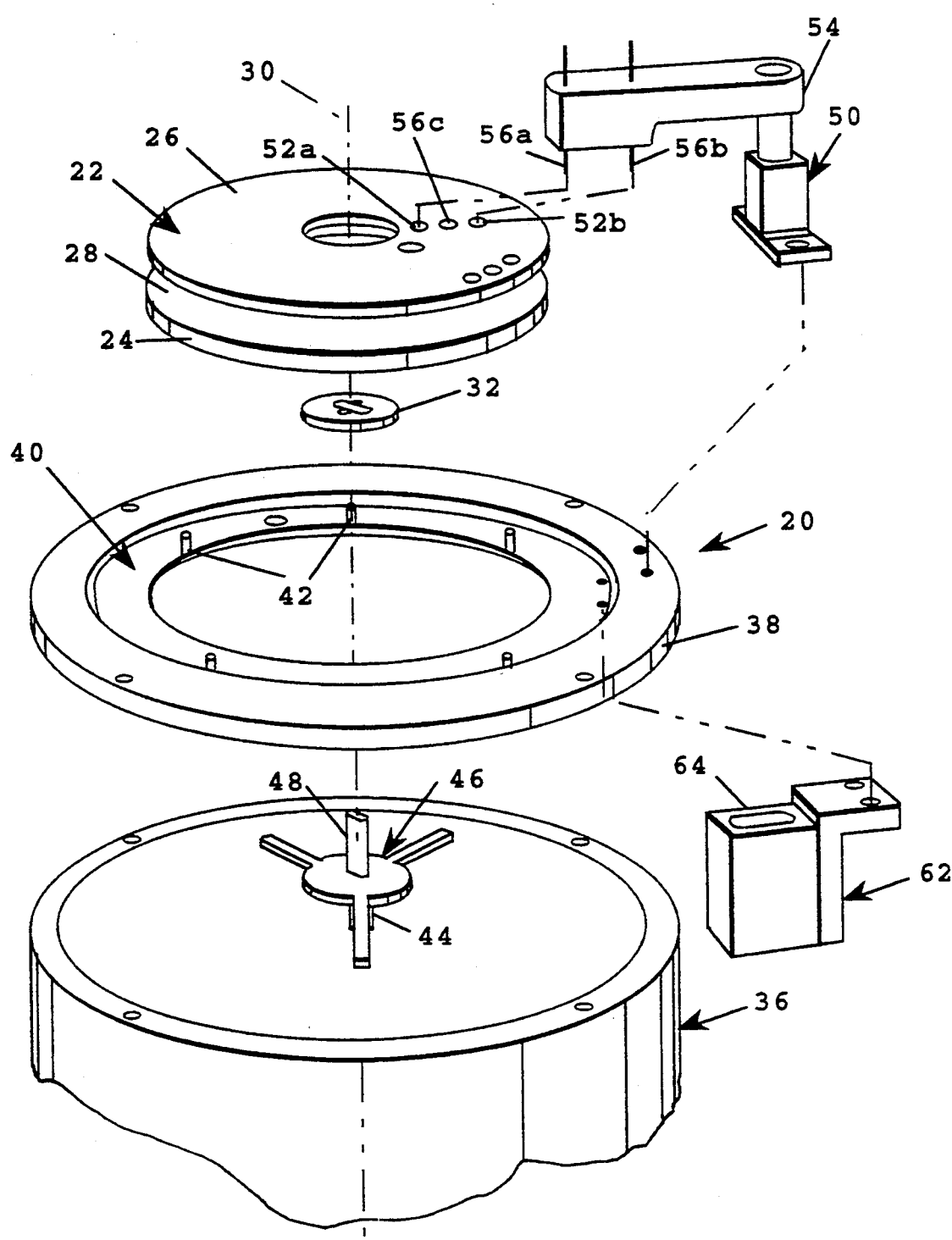
FIG. 1 is an exploded perspective view of the components in an assay apparatus constructed according to the present invention.

FIG. 1 illustrates, in exploded view, an assay apparatus 20 constructed according to the present invention. The apparatus includes an assembly 22 which also forms part of the invention and which will be detailed below with reference to FIGS. 2-12. Briefly, the assembly is formed of reaction and cover plates 24, 26, respectively which are joined together at their outer edges, and an intermediate transfer plate 28 which can be rotated relative to the two outer plates about a central axis 30. To this end, the transfer plate includes a hub 32 having an elongate opening 34 (FIG. 2) which is engageable for rotating the transfer plate, with the reaction and cover plates supported in a stationary position.

A control device 36 in the apparatus includes a base 38 which defines an annular seat 40 in which the assembly is supported during an assay operation. The base provides five pins, such as pins 42, arranged asymmetrically about the seat, as shown. These pins engage corresponding holes in the bottom of the assembly, described below, to immobilize the cover and reaction plates against rotation in the seat.

The base is supported on and attached to a drive motor which is indicated by a drive shaft 44 in the figure, the motor itself being contained with a motor housing. A three-arm support 46 attached to the end of the drive shaft has a projection 48 designed to engage the opening in hub 32, with the reaction surface of the assembly resting on the support arms, as can be appreciated in the figure. Thus, when the assembly is received and immobilized in seat 40, with projection 48 received in opening 34 in the hub, the intermediate transfer plate in the assembly can be rotated to selected positions with respect to the cover and reaction plates by the drive motor.

The motor in the control device can be moved from a lowered transfer position in which the assembly is immobilized in seat 40, as just described, to a raised free-rotation position in which the assembly is disengaged from the seat and is free to rotate on drive shaft 44. Because of a relatively high coefficient of internal (transfer plate) movement, the assembly can be rotated as a unit by the drive motor, such that the assembly and motor in a free-rotation position can function as a centrifuge to force material radially outwardly in the assembly, for a purpose to be described. The assembly can also be agitated, for mixing reaction components, by oscillating the assembly on the motor in a free-rotation position.

A wash unit 50 in the device is designed to circulate wash solution(s) through the assembly, as will be described below with respect to FIG. 10. Briefly, when the assembly is placed in a wash condition, openings 52a, 52b formed in cover plate of the assembly form the ends of a closed passageway which includes a portion of the reaction well in the assembly. Unit 50, which is mounted on base 38 as indicated, includes a vertically positionable arm 54 which holds a pair of tubes 56a, 56b, for insertion into openings 52a, 52b, respectively, when the arm is moved to a lowered, wash position. In a wash operation, wash solution is supplied through tube 56a under pressure, and is removed through tube 56b.

Also shown in FIG. 1 is a heating unit 62 in the apparatus used for heating a reaction well in the region in the assembly to selected reaction temperatures. The unit is attached to the lower side of base 38, as indicated, to position a heating element 64 in the unit directly below the reaction well in the assembly, with the assembly seated on the base.

Although not shown in FIG. 1, device 36 may also include an optical sensing unit for detecting analyte in the assembly. One preferred unit will be described below with respect to FIG. 11.

The assay assembly of the invention is illustrated particularly with respect to FIGS. 2-12. Reaction plate 24 in the assembly (FIGS. 2 and 5) provides an elongate, radially extending channel or well 66 which serves as the reaction chamber in the assembly, i.e., the chamber where the analyte and various reagents required for analyte binding and detection are brought into liquid contact with a solid-phase support contained in the well. In the embodiment shown, the well is formed in a metal, e.g., aluminum, insert 166 which is attached to the lower side of a disk-like plate member 168. The insert is carried below a platform 170 defined by the upper surface of plate member 168, above the insert. Formed in the platform are radially spaced openings 172a and 172b adjacent opposite end regions of the channel, and a central opening 172c. Openings 172a and 172b are aligned with openings 52a and 52b in plate 26, for a purpose to be described.

Figure 7A:
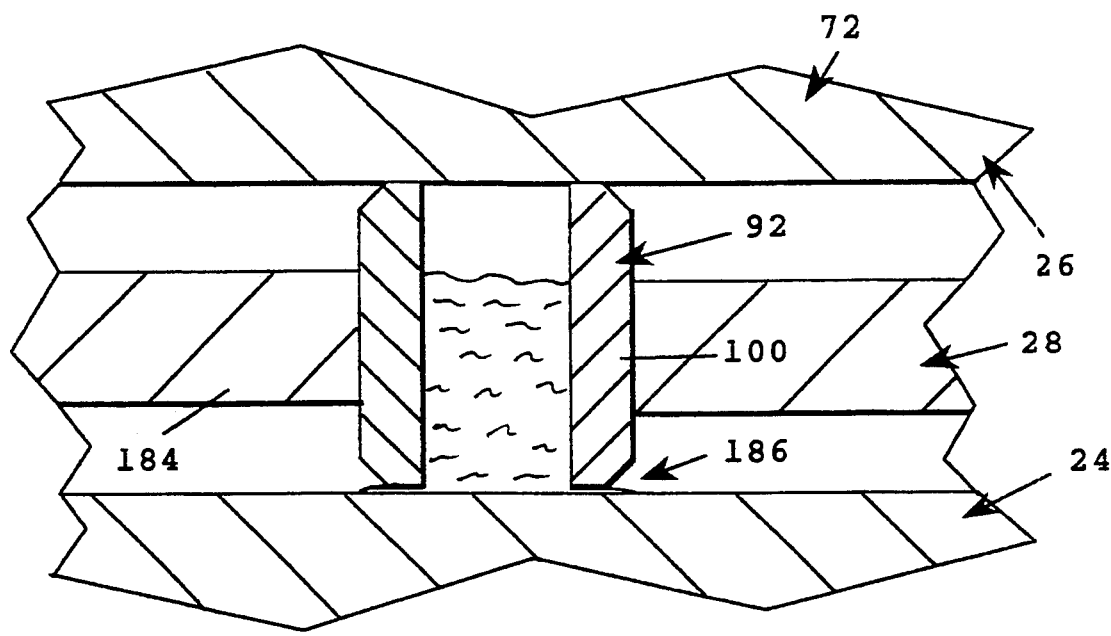
FIGS. 7A and 7B are enlarged, fragmentary sectional views of reservoir regions seen along lines A—A in FIG. 6A and along line B—B in FIG. 6B, respectively.
Figure 7B:
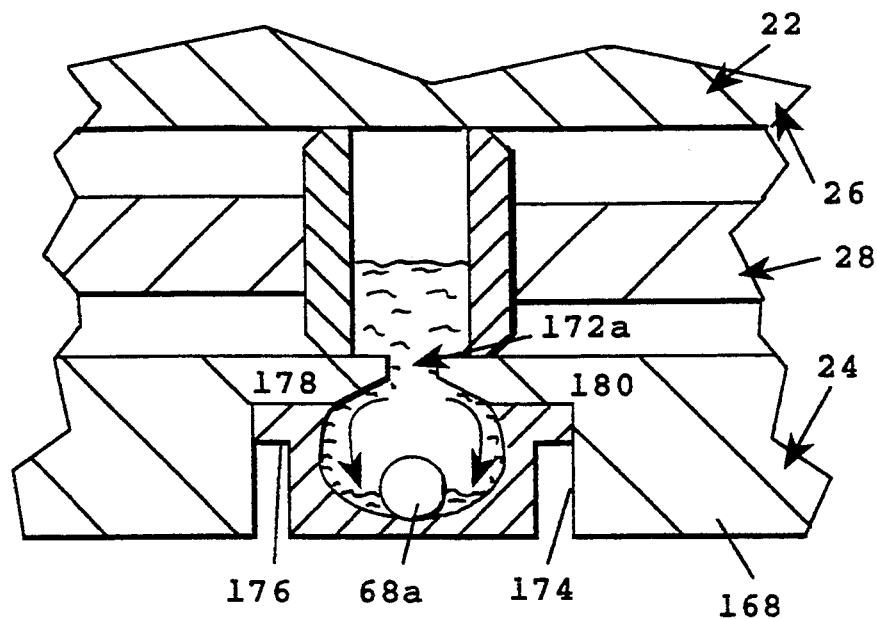

Details of the well construction in the plate are seen in FIG. 7B which shows an enlarged cross-section of the well region in plate 24 and overlying regions of plates 26, 28. The channel or well formed in the insert has a substantially U-shaped cross-section extending between opposite ends, corresponding to the regions below openings 172a and 172b in FIG. 5, with the outer radial end region of the channel forming a tapered ramp 70, as seen in FIG. 10. The insert is received in a cavity 174 formed in the lower region of plate member 168, and attached to the plate member by flanges, such as seen at 176. Each opening in platform 170, such as opening 172a shown in FIG. 7B, communicates with the well, and includes a short cylindrical-bore section 178 and a chamfered section 180. This construction serves to draw liquid into and through the opening from a reservoir in plate 28 into the channel in the reaction plate, as will be described below.

Carried in the channel are one or more solid-phase beads or particles, such as particles 68a, 68b, 68c, which form solid phase supports in the assay reaction. In the embodiment described in Section C below for solid-phase DNA determination, the three particles are for (1) positive control, (2) negative control, and (3) analyte binding. The channel and particles are shown in cross section in FIGS. 10 and 12A. The invention also contemplates a reaction format containing only a single solid-phase support.

Located just beyond the outer end of the channel in plate 24 is an arcuate groove 72 which serves as a guide for the particles, also for a purpose to be described. Adjacent this groove are three wells 74a, 74b, 74c into which the three particles may be transferred from channel 66 after the chemical reaction, also as will be described below. The three wells may contain a detection solution for detecting the presence of reporter molecules bound to the solid particles.

The reaction plate is secured to the cover plate by fasteners, such as rivets 75 (FIG. 2), connecting the outer annular rim regions of the two plates. The fasteners are received through holes, such as holes 76, formed in the plate. Also formed in the reaction plate is a central opening 82 through which projection 48 is received when the assembly is seated on the control device.

Figure 2:
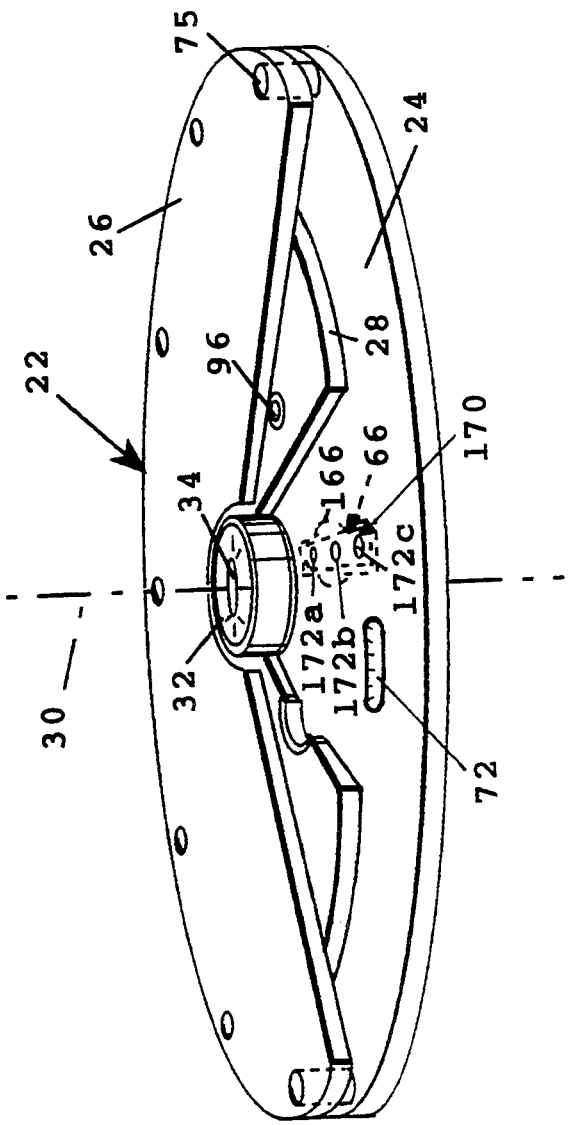
FIG. 2 is an enlarged, partially cutaway perspective view of an assay assembly constructed according to the invention.
Figure 3:
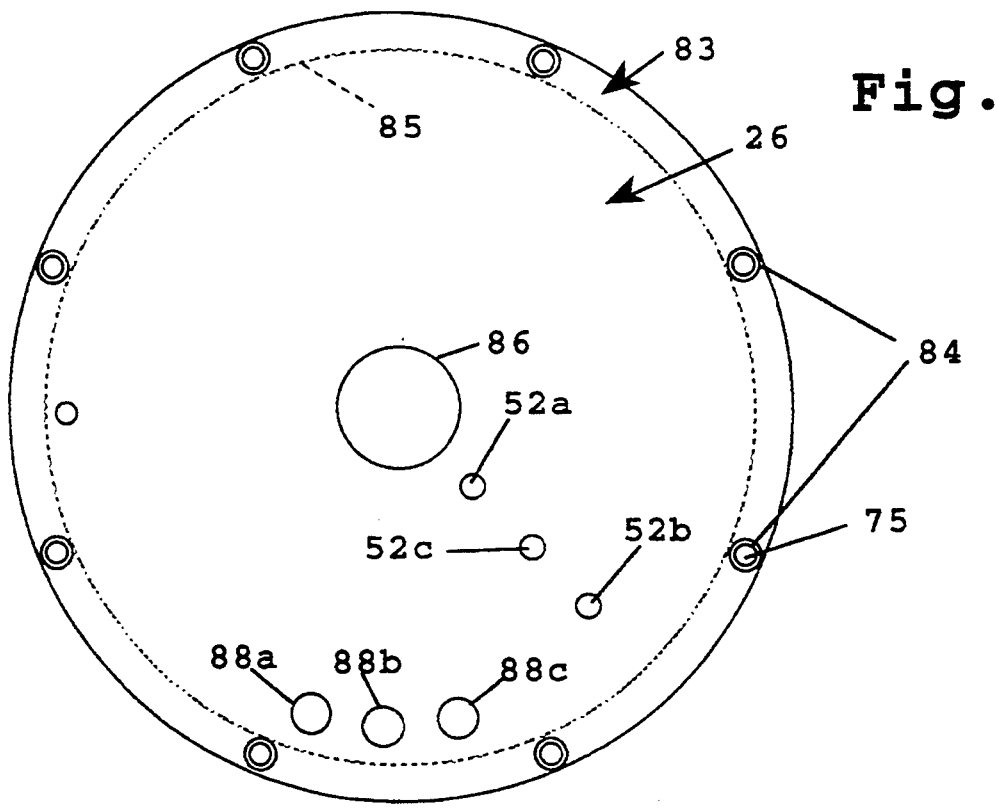
FIG. 3 is a plan view of a cover plate in the FIG. 2 assembly.

Cover plate 26 in the assembly is illustrated in plan view in FIG. 3. The plate is a circular disc having the same diameter as the reaction plate. Formed in an outer annular rim region 83 of the plate are holes, such as holes 84, for fastening an upper and reaction plates (dotted line 85 in FIG. 3 indicates the outer edge of transfer plate 28 in the assembly). Also formed in the cover plate are: (i) a central opening 86 through which the cover portion of hub 32 is received, as seen in FIG. 2; (ii) a series of windows 88a, 88b, 88c which are aligned with wells 74a, 74b, 74c, respectively, in the reaction plate; (iii) above described openings 52a, 52b, which are aligned with openings 172a, 172b, respectively, for circulating wash solution through the channel; and (iv) an opening 52c between ports 52a and 52b, in alignment with port 172c.

Figure 4:
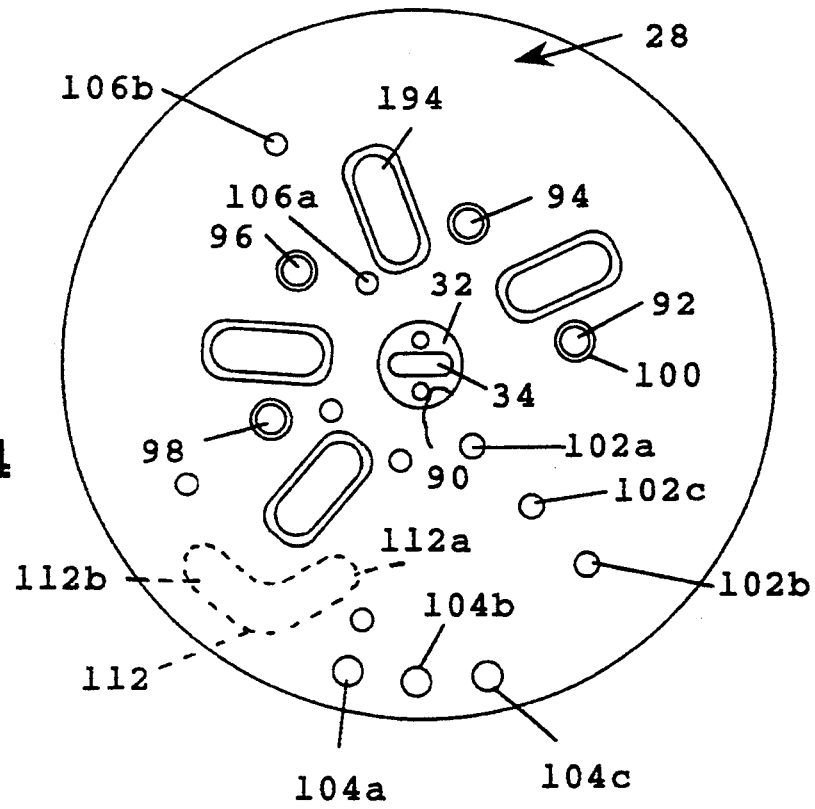
FIG. 4 is a plan view of a transfer plate in the FIG. 2 assembly.
Figure 5:
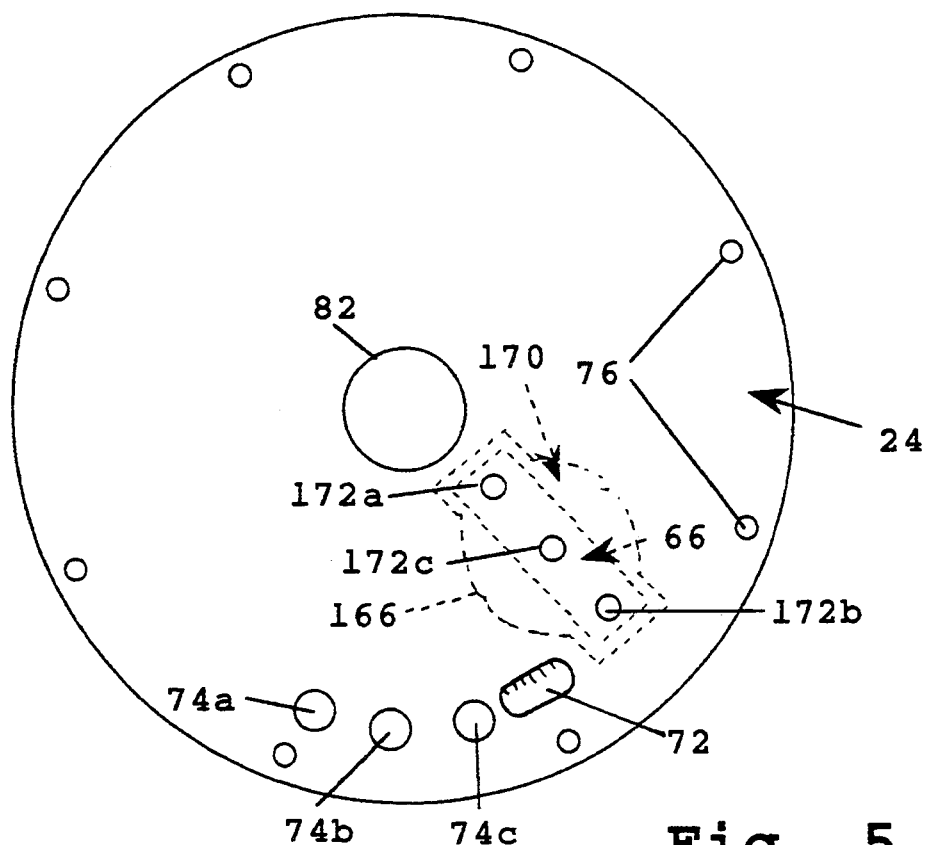
FIG. 5 is a plan view of a reaction plate in the FIG. 2 assembly.

With reference now to FIGS. 2 and 4, transfer plate 28 includes a plate member 190 having a central opening 90 in which hub 32 is fixed for rotation with the plate. The plate includes four reagent reservoirs 92, 94, 96, and 98 which take the form of cylindrical channels extending through the plate. With reference particularly to FIG. 7A, reservoir 92, which is representative, is formed of a sleeve 100 which extends through plate member 184, extending beyond the plane of the plate member on both upper and lower sides of the plate member. In the completed assembly, the sleeves forming the several reservoirs are axially compressed, forming liquid-tight seals against confronting faces of the cover plate and reaction plate, as illustrated in FIG. 7A. The sleeves are preferably formed of Teflon or polyethylene. The sealing ends of the sleeves are also referred to herein as means for preventing release of liquid reagent in a reservoir until the reservoir is aligned with one of the openings in the transfer plate communicating with channel 66.

The spacing between the plate member forming plate 28 and the confronting surfaces of the cover and reaction plates in the assembly function to prevent liquid contained in each reservoir from being drawn by capillarity into the gap between the two plates. That is, the gap between confronting plate surfaces, such as gap 186, is too great to produce capillary flow between the two surfaces. The gap in the embodiment shown is provided by the relatively greater lengths of the sleeves forming the reservoirs compared with the thickness of plate member 184. Alternatively, the region of the transfer plate member immediately adjacent each sleeve may be recessed to form a capillary-block gap around each sleeve.

Figure 6A:
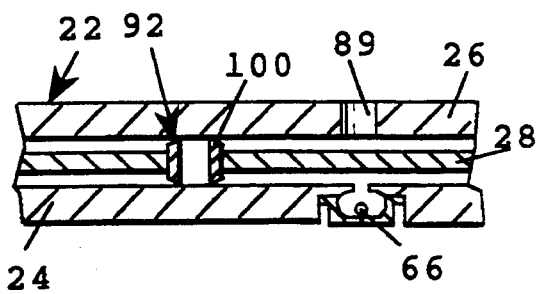
FIGS. 6A and 6B are fragmentary sectional views taken at relative plate positions in the FIG. 2 assembly at which a reagent reservoir in the transfer disc in the assembly is isolated from a reaction channel in the reaction plate (6A), and the reservoir is in a transfer position with respect to the channel (6B)

As just indicated, each of the reservoirs in plate 28 is alignable with one of the openings 172a–172c in the reaction plate communicating with channel 66, for delivering fluid reagents to the reaction chamber, to be described below with reference to FIGS. 6A, 6B and 7B. In particular, it is noted that some of the reservoirs, such as reservoirs 94, 96, and 98 are radially spaced, preventing cross-contamination of liquid reagents in the two reservoirs, as the reservoirs are moved relative to the cover and reaction plates.

Also formed in transfer plate is an openings 102a–102c alignable with opening 172a–172c, respectively, in the reaction plate and at the same time with openings 52a–52c in the cover plate. Any of the three sets of alignable openings are referred to herein collectively as means for introducing sample into the assembly's reaction region.

Other openings formed in the transfer plate include three windows 104a, 104b, 104c which are alignable with windows 88a, 88b, 88c, respectively, for viewing wells 74a, 74b, 74c, respectively, when the two sets of windows are aligned. In addition, the transfer plate provides three sets of radially spaced openings, such as openings 106a, 106b, which are alignable, at one of three different plate positions, with openings 172a, 172b, respectively, in the reaction plate, at the same time, with ports 52a, 52b in the cover plate, for forming a continuous passageway 108 (FIG. 10) for circulating wash solution through the reaction region.

Figure 8:
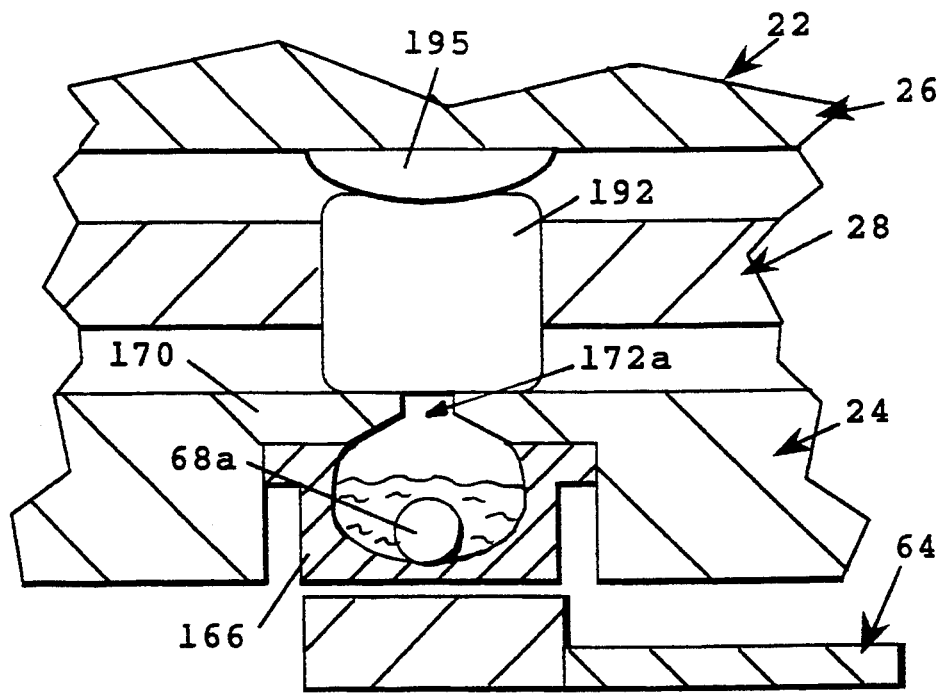
FIG. 8 is an enlarged, fragmentary sectional view of sealed well in the assembly, during a heating step in the operation of the assembly.
Figure 11:
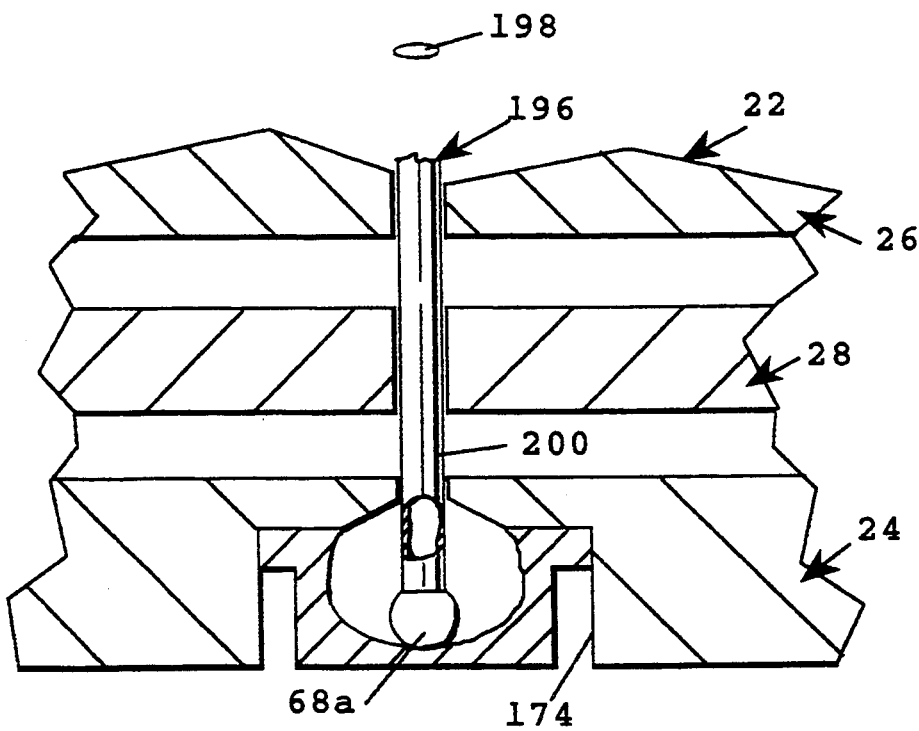
FIG. 11 is an enlarged sectional view of a well region of the assembly, showing detector structure for detecting an optical signal from a bead in the well.

The transfer plate also includes a plurality of floating sealing pads, such as pads 192, 194, which are designed for sealing the channel openings in the reaction plate, when the liquid contents of the reaction plate are heated. Details of the operation of the pads in a heating operation are seen in FIG. 8. Shown here are an enlarged sectional view taken through the assembly in the region of the reaction channel, and a portion of heater element 64 used in heating the liquid contents in the channel. As seen, the heating element makes contact with the lower side of insert 166 during heating.

Pad 192, which is representative, is an elongate elastomeric pad, such as formed from polyethylene or other compressible, low-friction polymer material, which is dimensioned to cover openings 172a–172c, when the pad is positioned on platform 170, as indicated in FIG. 8. The pad is carried in a radially extending slot 194 formed in the transfer plate member, for floating in a direction normal to the plane of the plate. The pad's height dimension allows the pad to be moved easily and without pad compression, between the cover and reaction plates, as the transfer plate is rotated relative to the other two plates. However, as the pad is moved toward a sealing position above the reaction well, it makes contact with a radially extending cam member 195 formed on the lower side of the cover plate, immediately above openings 172a–172c. As can be appreciated from FIG. 8, this contact acts to bias, i.e., compress, the pad against the platform openings, sealing the openings to the reaction well.

The transfer plate also provides an L-shape slot 112 formed in its lower side, i.e., the side confronting the reaction plate. The slot includes radially and circumferentially extending portions 112a, 112b which are alignable with the outer end region of channel 66 and groove 72 in the reaction plate, respectively. The slot is positioned and dimensioned to receive the particles from channel 66 (FIG. 12A) as will be described in Section B.

The plates in the assembly are preferably formed by injection molding of a suitable plastic. For forming the transfer plate, plate member 184 can be injected molded about the four sleeves forming the four reservoirs in the transfer plate, and hub 32, and subsequently fitted with the four sealing pads. For forming the reaction plate, plate member 168 can be injected molded about insert 166. With the transfer plate placed between the cover and reaction plates, the two outer plates are secured together, such as by rivets, glue or heat welding. As noted above, construction and plate attachment is such as to bias the cover and reaction plates firmly against confronting sides of the transfer plate, to compress the elastomeric seals in the assembly. Liquid reagent can be added to the reservoirs and wells by suitable positioning of the transfer plate after assembly.

Figure 9A:
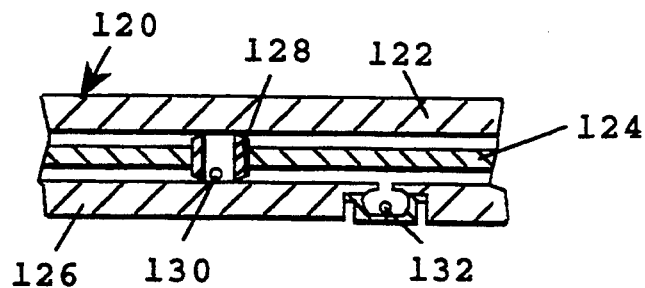
FIGS. 9A and 9B are sectional views similar to 6A and 6B, respectively, but illustrating an embodiment of an assembly in which the reagent in the reservoir is in dried particle form.
Figure 9B:
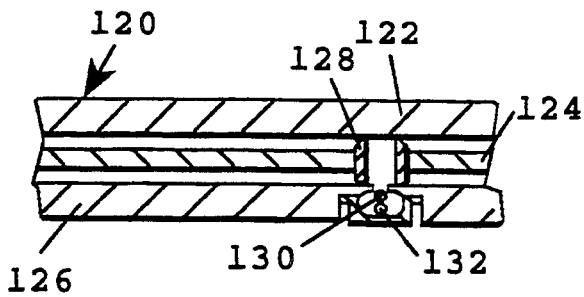

In another general embodiment of the assembly, the reagent reservoirs are designed for delivery of a dehydrated reagent particle composed of the dried reagent, preferably formulated in pelletized form. This embodiment is illustrated in FIGS. 9A and 9B which shows a fragmentary portion of an assay assembly 120, with cover plate 122, transfer plate 124, and reaction plate 126. The cover and reaction plates in the assembly are substantially identical to those in assembly 22. The transfer plate includes a plurality of reservoirs, such as reservoir 128, which communicate with the reaction plate, but not the cover plate.

Each reservoir contains a dried reagent particle, such as particle 130 in reservoir 128, which is held within the reservoir, for deposit into reaction channel 132 in the reaction plate, when the reservoir is aligned with the transfer plate, as seen in FIG. 9B. The lower end of the reservoir is sealed by the sleeves forming the reagent reservoirs, to prevent exposure of the reagent to moisture or contamination by other reagents.

The pelletized reagent may be formulated, if desired, with a variety of water-soluble bulking agents, such as water-soluble polymers, according to well-known methods. Where the assembly includes one or more solid-phase particles, these are added to the reaction channel in the reaction plate before the transfer and reaction plates are joined.

The assemblies described and illustrated above are designed particularly for use in a solid-phase DNA analyte assay involving (i) at least one solid-phase particle, (ii) four separate liquid and/or solid reagents which are added sequentially, (iii) a heating step following each reagent addition, and (iv) three individual wash steps which follow the addition of the second, third, and fourth reagents, as will be described below.

A variety of alternative assembly configurations are contemplated in the present invention. For example, the assay may involve sequential addition of two reagents, requiring only two reservoirs, or two or more of the reagents may be added to the reaction region simultaneously, in a configuration in which the reservoirs are carried along a common radial line.

Further, the solid-phase particles in the reaction may be replaced by one or more separate solid-phase supports formed on the channel wall, and/or the solid phase particles may be carried within separated wells in the reaction chamber, obviating the need for particle transfer after the assay reaction. Alternatively, the assay reaction may occur in a liquid phase, either in a free solution or in a absorbent filter, eliminating wash steps. In the case of an absorbent-filter type reaction region, a liquid reagent may be drawn onto the filter by wicking or capillarity, eliminating the need for venting liquid-carrying reservoirs.

B. Operation of the Assembly and Apparatus

In operation, the assembly is placed in the seat of the control device, with the pins of the device being received in the corresponding holes in the assembly reaction plate, and with projection 48 being received in hub 32, as described above. Hub 32 is initially oriented with respect to the pins such that the transfer plate is in a home position at which all of the reservoirs and the reaction region are sealed.

Figure 13:
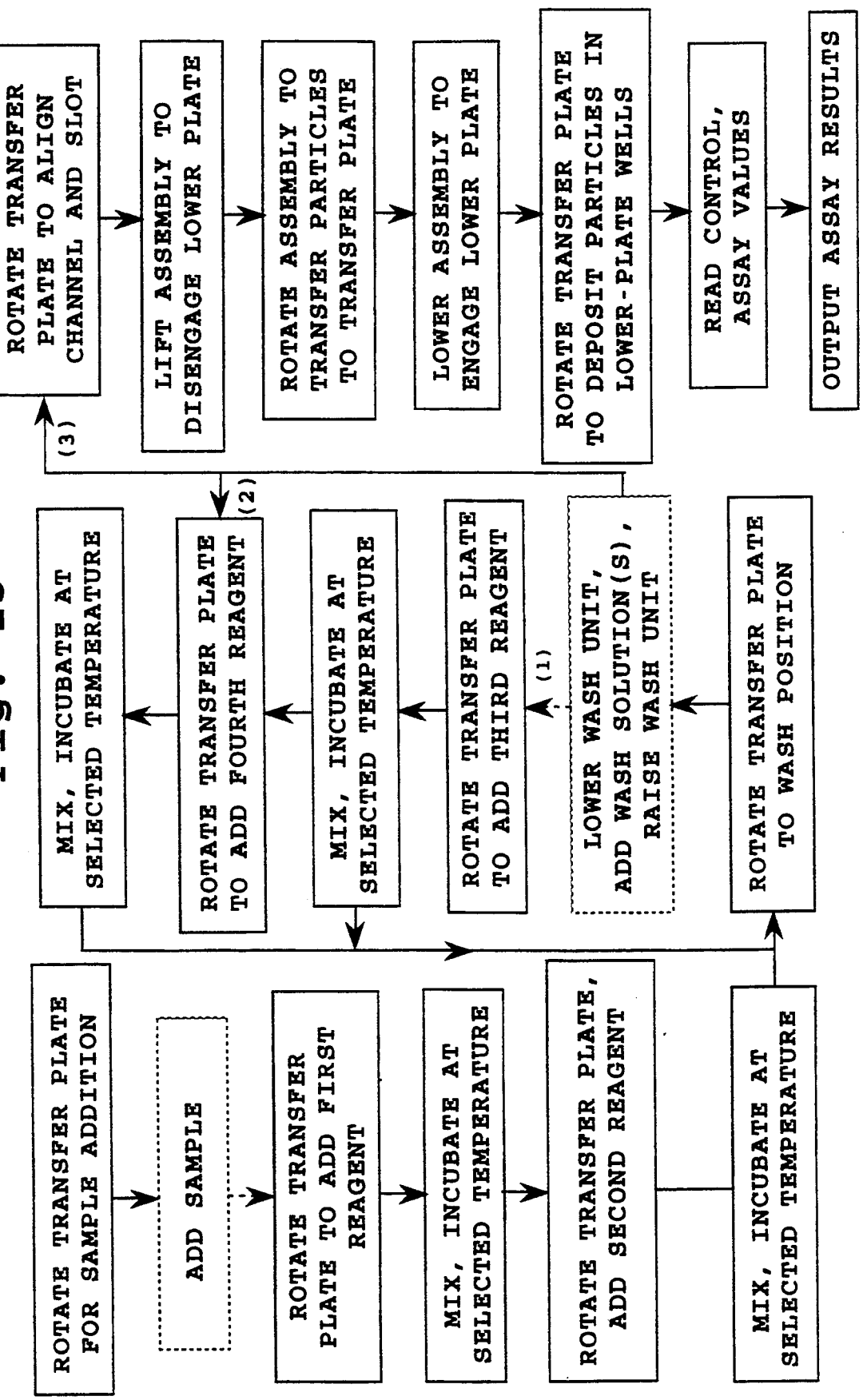
FIG. 13 is a flow diagram of the steps carried out by the apparatus in executing an exemplary analyte assay.

The following exemplary operation will be described with reference to FIG. 13, which is a flow diagram of the assay steps in the DNA-analyte assay described in Section C below. The steps shown in solid-line boxes are preferably executed in an automated fashion by a suitable microprocessor control unit (not shown) in the control device. The sample and/or wash-solution addition steps shown in the dashed-line boxes may be performed either manually or under the control of the apparatus.

The control device is first actuated to move the transfer plate in a clockwise direction in FIG. 2, to align opening 102a in the transfer plate with opening 52a in the cover plate and opening 172a in the reaction plate, and a liquid sample is introduced through the aligned opening into the reaction channel. The analyte sample may be any fluid sample, such as a blood, serum, or plasma sample, in a suitable amount, typically between about 10–200 μl.

Figure 6B:
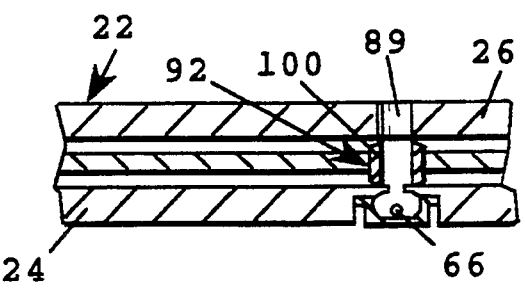

The transfer plate is rotated further in the same direction to align reservoir 92 with opening 172a in the reaction plate, as shown in FIGS. 6B and 7B, to transfer the liquid reagent in the reservoir into the channel. As the reservoir seal first overlaps the edge of opening 172a, the fluid seal in the reservoir is broken, allowing fluid to flow readily out of the reservoir. As discussed above, the capillary lock feature of the transfer plate prevents the fluid from flowing by capillarity out of the reservoir into the region between transfer and reaction plates. The chamfered opening 172a serves to direct fluid from the reservoir into the well by a combination of capillarity, provided by narrower upper section of the opening, and rapid fluid flow provided by the lower chamfered section of the opening.

As mentioned above, in an alternative embodiment of the invention, the reservoir may contain a dehydrated, pelletized reagent which is deposited by gravity into the reaction channel, as indicated in FIG. 9B. To mix the reagent with the liquid sample, the transfer plate may be rotated back to a channel sealing position, the assembly lifted from the seat in the control device, by raising the drive motor to a free-rotation position, and the assembly is oscillated slowly as a unit by the motor.

After introducing the liquid (or solid) reagent into the reaction well, the transfer plate is rotated slightly to position pad 192 over the reaction well. As described with respect to FIG. 8, the pad at this position is compressed between the cover and reaction plates, forming a tight seal about the reaction well. The heating element in the device is then activated to heat the well for a selected reaction period. During the heating cycle, heated fluid from the reaction mixture is prevented from escaping from the well by the seal over openings 172a–172c.

The transfer plate is now rotated to transfer the contents of reservoir 94 into the channel, and the reaction mixture is again mixed and reacted for a given reaction period at a selected temperature. As can be appreciated with reference to FIG. 4, continued movement of the transfer plate in a clockwise direction aligns the first set of wash-solution ports, indicated at 106a, 106b with openings 52a, 52b, respectively, in the cover plate, and openings 172a, 172b, respectively in the reaction plate. When this alignment is achieved, the wash unit is lowered to insert the wash-solution tubes into the aligned ports, and wash solution is circulated through the reaction channel as illustrated in FIG. 10, to wash the initial sample and first two reagents from the reaction chamber.

The above steps are repeated to (i) transfer, mix and incubate a third reagent with the washed solid-phase particles in the reaction chamber, (ii) remove the third reagent by washing, (iii) transfer, mix and incubate a fourth reagent with the washed particles, and (iv) remove the fourth reagent by washing. These steps are shown in FIG. 13, where the three separate wash steps are indicated at (1), (2), and (3).

After completing the reaction, an analyte-dependent signal on the solid-phase surface, i.e., the solid-phase beads, may be read with the beads in the reaction well. In order to minimize optical-reading artifacts from the other beads in the reaction well, the signal detector in the device (or in a separate optical reading device) preferably has a construction like that shown for detector 196 in FIG. 11, allowing direct reading of each bead. The detector includes an optical sensor 198 and a refractory tube 200 dimensioned to cover a segment of the sphere as indicated, when the tube is lowered through an opening in the assembly (formed by a opening in the cover, transfer, and reaction plates) into the reaction well. After each bead is read, the tube is raised and then lowered into another assembly opening to read the next bead.

Figure 12A:
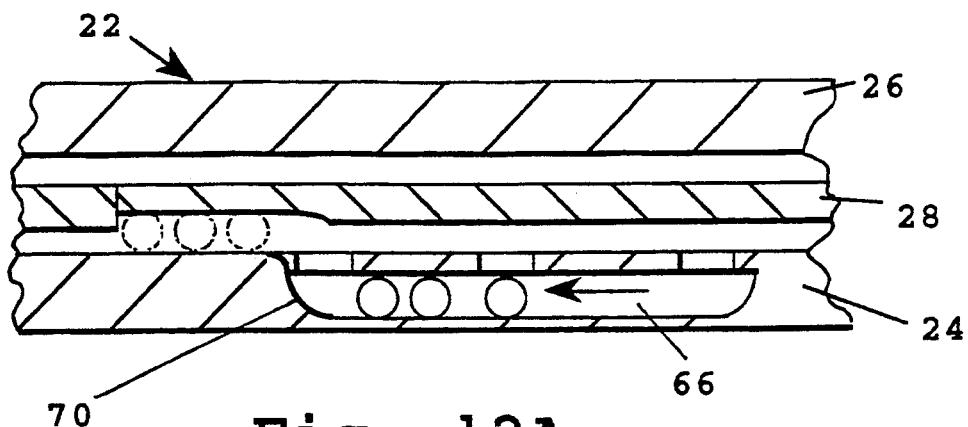
FIGS. 12A-12C illustrate the steps in transferring solid-phase particles from the reaction channel in the reaction plate into a slot formed in the transfer plate (12A, 12B), and from this slot into separate wells in the reaction plate (12C)
Figure 12B:
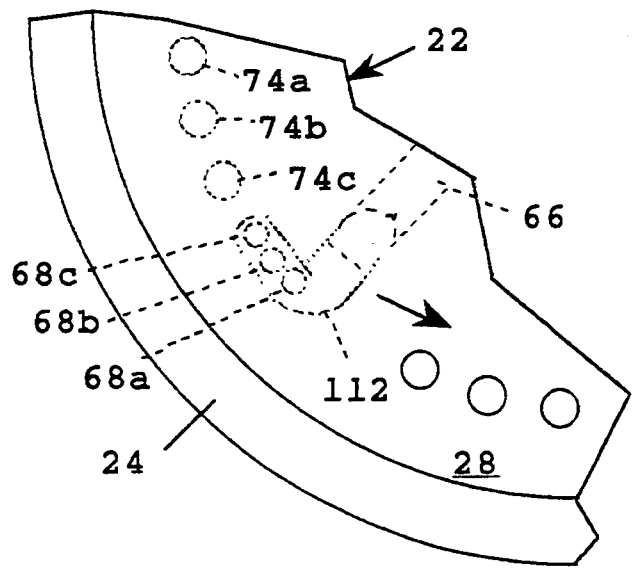
Figure 12C:
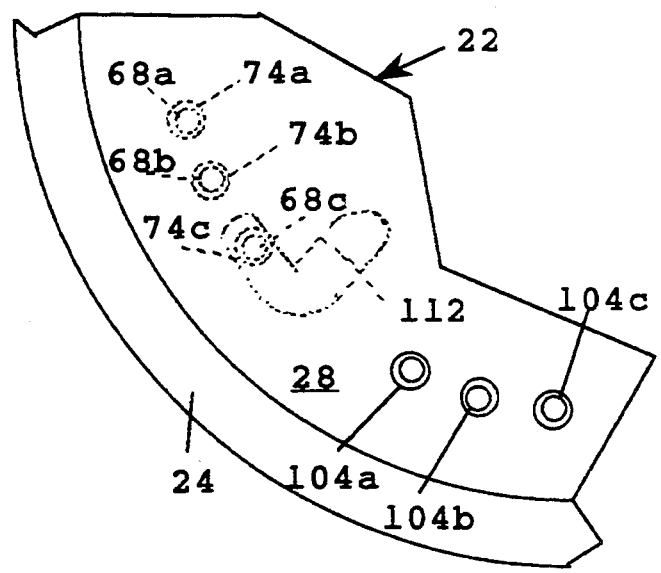

Alternatively, the beads may be distributed into separate reading chambers, according to the operation following described with respect to FIGS. 12A–12C. Briefly, the transfer plate is rotated to the position shown in FIG. 12B to align the radial portion of slot 112 with the reaction channel. With the drive motor moved to its raised position, the assembly is now rotated at a speed sufficient to force the particles in the reaction channel radially outwardly into the slot, as shown in FIG. 12A. The particles are forced ultimately into the circumferential portion of the slot, as shown in FIG. 12B. The particles are captured in groove 72 (FIG. 5) at this position, to prevent their return to the reaction channel at the end of centrifugation.

To distribute the particles into the respective wells in the reaction plate, the motor is moved to its lowered position, the assembly reseated on the control device, and the transferred plate rotated in a clockwise direction, i.e., in a direction which tends to force the particles toward the back of the slot (the particle positions shown in FIG. 12B). As the slot is moved over each well in the reaction plate, the forwardmost particle in the slot drops into that well, until particle transfer into all three wells is completed.

The amount of analyte associated with each of the solid phase particles may be determined by a variety of known methods. Typically, the analyte, which is specifically bound to the particle, itself binds a label probe (reporter molecule) which contains fluorescent, or enzyme reporter moieties which can be detected and/or quantitated by standard photodetector or spectrophotometric means. As indicated above, the wells may contain a detection solution which is reactive with the reporter moieties to produce the desired detection signal.

One advantage of the particle transfer feature of the invention is that several solid-phase particles can be reacted under identical conditions in a single chamber, then isolated for detection. The separation of the particles for detection allows accurate detection by chemiluminescence, fluorescence, or enzyme activity which is not possible when the particles are closely spaced and/or in the same reaction chamber. However, it will be recognized that the invention is also advantageous for carrying out a solid-phase reaction employing one or more beads, or other solid-support surfaces in the reaction well, and reading the solid surfaces in the well, as described with respect to FIG. 11.

Section C below describes an exemplary assay method for detection of analyte DNA by a solid-phase reaction method. The method is illustrates various advantages of the assembly and apparatus, including (i) the ability to carry out complex, multiple reagent assays in a simple, self-contained assembly, (ii) quantitative reagent transfer from the transfer plate to the reaction plate, (iii) the ability to intersperse reaction steps with wash cycles, (iv) the ability to carry out heated incubation steps without liquid loss, and (v) the ability to conduct multiple solid phase reactions in a single chamber, then separate the solid-phase supports for analyte detection. Although the DNA analyte assay is illustrative of one type of assay which may be carried out in the assembly and apparatus of the invention, it will be understood that the invention is readily adapted to a wide variety of assay procedures in which solid or liquid reagents are to be added to a reaction region, preferably sequentially, for detection or quantitation of an analyte in a reaction zone.

In particular, the invention contemplates detecting a ligand analyte in which the solid-support surface in the reaction well includes molecules which bind specifically with the ligand, or which can bind specifically to the ligand through a bivalent intermediate molecule provided by way of one of the added reagents. In a preferred format, the ligand is an antigen, and the ligand-binding molecule carried on the solid support is a ligand-specific antibody. After addition of a ligand-containing sample to the solid support, and a wash step to remove unbound sample material, a first reporter reagent is added to the well. This reagent contains a reporter-labeled molecule capable of binding specifically to the ligand, with such bound to the solid support. Following a second wash step to remove unbound material, a second reagent containing a substrate for detection of the bound reporter is added to the reaction well. Preferably the reporter is an enzyme, such as alkaline phosphatase or peroxidase, and the second reagent contains substrate capable of reacting with the enzyme reporter to produce a detectable color reaction in the reaction well.

In both the DNA probe format, and the ligand format just described the multiple reagents carried in the assembly for producing analyte-specific binding to the solid support, and detectable signal of the bound analyte are referred to herein, collectively, as reaction reagents required for binding of analyte to the solid support in detectable form.

It will be appreciated that the assembly of the invention may be manually operated, particularly where the assembly has a simplified format in which reagents are added to a liquid reaction chamber, for production of an analyte-dependent signal in a liquid-phase. Here the user can readily manipulate the assembly to its reagent transfer positions, and perform any necessary mixing by manual shaking.

C. Solid-Phase Assay for DNA

FIGS. 14A–14D illustrate schematically the sequence of reaction steps in a solid-phase DNA analyte assay carried out using the assembly and apparatus of the invention.

Considering first the solid-phase particles and reagents which are included in the assembly, the three solid-phase particles serve as positive and negative controls (particles a and b) and for specific analyte assay (particle c). The negative-control particle is uncoated and the positive-control and analyte particles are coated with single-stranded DNA fragments which are complementary to positive-control and analyte-specific capturing probes, respectively. The nature of these probes is described below. The positive-control and analyte particles are prepared by derivatizing polymer or glass beads with the selected DNA fragments, according to standard coupling methods. The analyte solid-phase particle is indicated at 130 in FIGS. 14A–14D, and the DNA fragments coating this particle which are complementary to the analyte probes are indicated by dashed lines, such as at 132.

A first liquid reagent, contained in reservoir 92 in the assembly, includes a denaturation agent, such as NaOH, positive-control and analyte-specific capturing probes, a positive-control DNA, and positive-control and specific amplifier probes. The positive-control DNA is a duplex DNA fragment which has a number of known sequence regions which are unique to that fragment, i.e., not present in the analyte DNA. The amplifier probes include a series of probes having a first region which is complementary to one of several different sequences in the positive control DNA and in the analyte nucleic acid, and a second, common region which is complementary to a sequence in a branched DNA contained in the third reagent. In the amplifier probe illustrated at 134 in FIG. 14A, a first region which is complementary to a sequence in an analyte nucleic acid is indicated by a square-wave pattern at 136, and a second common region, indicated by coiled line 138, which is complementary to the sequence in the DNA on a branched DNA.

The positive-control capturing probes include a series of probes which have a common first-sequence which is complementary to a sequence in the DNA fragment carried on the positive control particle, and different second sequences which are complementary to different known sequence regions in the positive-control DNA. The analyte capturing probes similarly include a series of probes which have a common first-sequence which is complementary to a sequence in the DNA fragment carried on the analyte particle, and different second sequences which are common to the different known sequence regions in the analyte nucleic acid. One such analyte capturing probe is illustrated at 140 in FIG. 14A, which shows a first region, indicated by a sawtooth pattern at 142, which is complementary to a sequence in an analyte nucleic acid, and a second common region, indicated by dashed line 144, which is complementary to the sequence in the DNA carried on the analyte particle.

A second liquid reagent, contained in reservoir 94, includes an annealing agent or buffer which allows DNA annealing, such as by neutralizing a base denaturation reagent.

Figure 14A:
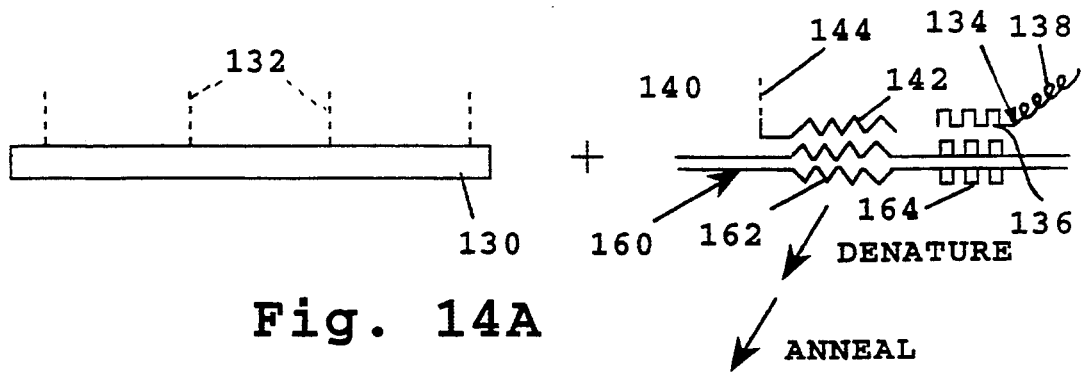
FIGS. 14A-14D are schematic illustrations of the sequential nucleic acid binding reactions in a DNA analyte assay which can be carried out in an automated fashion by the apparatus of the invention.
Figure 14B:
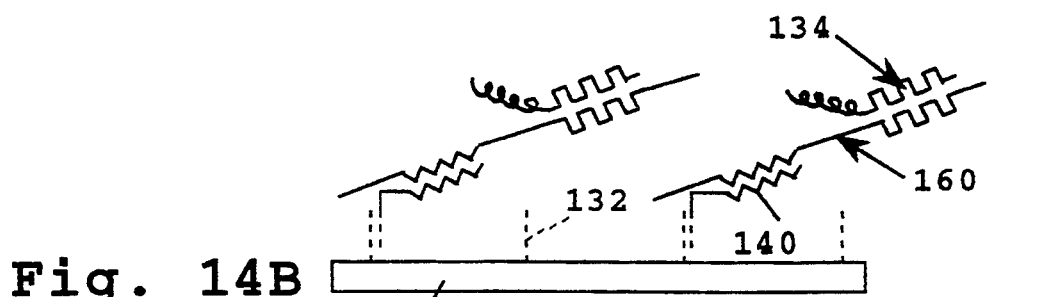
Figure 14C:
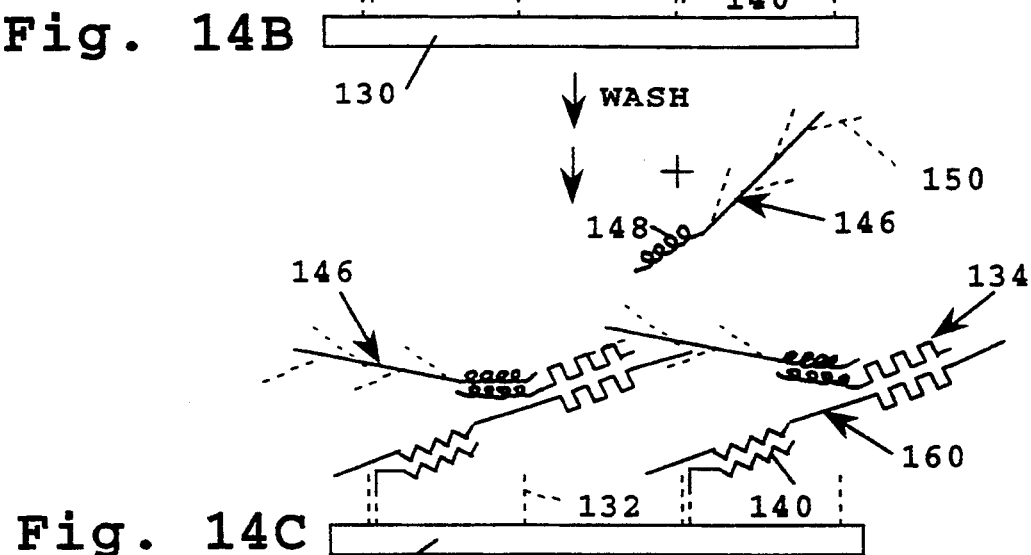
Figure 14D:
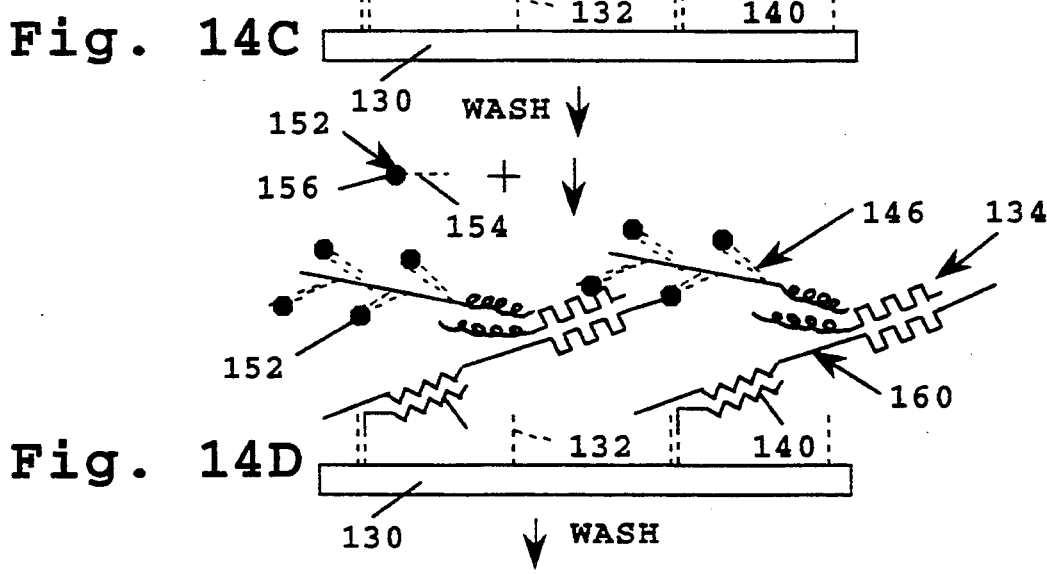

A third liquid reagent, carried in reservoir 96, includes the above-mentioned branched DNA molecule, which is indicated at 146 in FIGS. 14B–14D. The molecule includes a sequence indicated by coiled region 148, which is complementary to region 138 of the binding probes, and a group of branched-chain sequences, such as that indicated by dotted line 150, which are complementary to a label probe sequence. In this embodiment, the branched DNA is adapted for indirect binding to analyte and positive control nucleic acid, i.e., through the amplifier probes. Alternatively, the branched DNA may be designed for direct hybridization to sequences in the analyte and positive-control nucleic acid.

A fourth liquid reagent, contained in reservoir 98, includes a labeling probe, indicated at 152 in FIGS. 14C–14D, which includes a DNA fragment moiety 154 with a nucleotide sequence complementary to sequence 150 in the branched DNA molecule, and a reporter moiety 156 which is used for signal detection.

The reporter moiety in the present assay assembly is preferably an enzyme, such as alkaline phosphatase, which can generate a chemiluminescent signal in a suitable detection solution.

Completing the description of the chemical components of the assembly, the wells in the assembly are partially filled with a detection solution which are reactive with the reporter moiety to generate a detectable signal. For example, a solution containing doxetane is reactive with an alkaline phosphatase reporter moiety to generate a chemiluminescent signal which can be detected and quantitated with a photomultiplier conventionally.

Initially the assembly is positioned for sample addition and a sample containing a DNA analyte 160 is added to the assembly's reaction chamber. As indicated above, the analyte includes multiple sequences, such as sequence 162, which are complementary to regions of the analyte capturing probes in the assay, and one or more sequences, such as sequence 164, which are complementary to the binding probes in the assay.

After sample addition, the assembly is manipulated to add and mix the first reagent, then incubated for 10 minutes at 65° C. to denature the analyte. With addition of the annealing buffer, mixing, and further incubation for 10 minutes, the following probe-mediated binding reactions occur: (1) positive-control capturing probes hybridize with the positive-control particle and with the positive-control DNA to link this DNA to the positive-control particle; (2) amplifier probes hybridize with the positive control DNA; (3) analyte capturing probes hybridize with the analyte particle and with the analyte to link analyte DNA to the particle; and (4) amplifier probes hybridize with the analyte DNA. Steps (3) and (4) are illustrated in FIG. 14B.

After the annealing reaction, the assembly reaction chamber is manipulated for one or more wash steps in which wash solution is circulated through the reaction channel to remove unbound reagents. The third reagent is now added, mixed, and allowed to anneal at 55° C., to hybridize the branched DNA with particle-bound amplifier probes, as is illustrated in FIG. 14C. Following annealing, unbound branched DNA is removed by a second wash step.

The final labeling probe is added to the particles, mixed and allowed to anneal with the bound branched DNA, to bind reporter molecules to the positive-control and analyte particles. Binding of the labeling probe molecules to the analyte particle is illustrated in FIG. 14D. Unbound labeling probe is then removed by a third wash step, as indicated.

Figure 10:
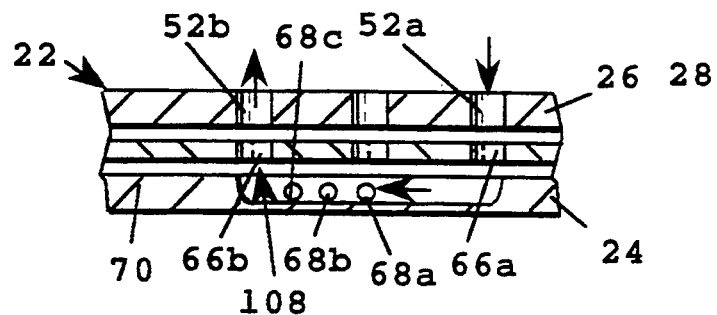
FIG. 10 is an enlarged, fragmentary sectional view of the assembly showing the assembly in a position for irrigating the assembly well.

The assembly is now manipulated by the steps shown at the right in FIG. 10, and described above, to transfer the three particles into the respective wells for signal detection. Reaction of the bound reporter with the detection fluid in the wells produces a detectable chemiluminescent signal which is measured and converted to a quantitative assay value which is displayed. In the three particle assay, the positive-control value is used to calculate a standard curve of analyte concentration as a function of concentration, with background (negative control) subtraction. Analyte concentration is determined from the standard curve, after background subtraction.

The assembly and apparatus provide several advantages in a solid-phase DNA assay, as can be appreciated. The assay can be carried out in a substantially automated fashion, and without addition of reagents from external sources. Accordingly, a minimum of laboratory training and user manipulations are required.

The ability to carry out multiple solid-phase reactions in a single chamber minimizes variations in quantitative analyte measurements due to variations in reaction conditions, allowing self-corrected analyte determinations based on a standard curve with background subtraction.

Although the invention has been described with respect to certain embodiments, configurations, and applications, it will be apparent to those skilled in the art that various changes and modifications may be made without departing from the invention.

It is claimed:

1. A self-contained assembly for detecting an analyte ligand by detectable, analyte-specific binding to a solid support, comprising a reaction plate defining a well that contains a solid support, said well being capable of holding liquid reagents in contact with the support, adjacent the reaction plate, a transfer plate containing first and second reagent reservoirs, each said reservoir being formed by an elastomeric sleeve held in a channel which extends through the transfer plate, said transfer and reaction plates being spaced relative to one another, in the region of the sleeve, to form a capillary lock effective to prevent liquid from leaking from the reservoir by capillarity, carried in said first and second reservoirs, first and second reaction reagents, respectively, required for binding of ligand in detectable form to the solid support, and means for mounting the transfer plate on the reaction plate for movement thereon to a sample-addition position at which sample can be added to said well, a first reagent-transfer position at which the first reservoir is aligned with said well, a wash position at which wash solution can be introduced into the well, and a second reagent-transfer position at which the second reservoir is aligned with said well, wherein said sleeve is effective to prevent release of each said reagent from its respective reservoir until that reservoir is aligned with said well.

2. The assembly of claim 1, wherein at least one of said first and second reagents is in the form of a liquid solution.

3. The assembly of claim 1, which further includes a cover plate secured to the reaction plate, said cover plate having ports which are alignable with said reservoirs when the transfer plate is in one of said first and second reagent transfer positions, and said sleeve is effective to form a seal between the transfer plate and both the reaction and cover plates.

4. The assembly of claim 1, wherein the reaction plate includes a chamfered opening disposed above said well for communicating said reservoirs in the transfer plate with the well in the reaction plate.

5. The assembly of claim 1, wherein at least one of said first and second reagents is a pelletized reagent, and the pelletized reagent is delivered from one of said first and second reagent reservoirs to said well by gravity, when said one reagent reservoir is aligned with the reaction well.

6. The assembly of claim 1, wherein said mounting means allows rotation of the reaction and transfer plates relative to one another.

7. The assembly of claim 1, for use in an immunoassay for detection of a ligand effective to bind immunospecifically to the solid support, wherein said first reaction reagent includes an antiligand reagent capable of binding immunospecifically with such ligand, when the ligand is bound to the support, and said second reaction reagent includes a reagent capable of reacting with the antiligand reagent to produce a detectable signal on the solid support.

8. A self-contained assembly for detecting an analyte ligand by detectable, analyte-specific binding to a solid support, said assembly being intended for use with a heater effective to heat the well in the assembly, said assembly comprising a reaction plate defining a well that holds a solid support, said well being capable of holding liquid reagents in contact with the support, adjacent the reaction plate, a transfer plate containing first and second reagent reservoirs, carried in said first and second reservoirs, first and second reaction reagents, respectively, required for binding of ligand in detectable form to the solid support, means for mounting the transfer plate on the reaction plate for movement thereon to a sample-addition position at which sample can be added to said well, a first reagent-transfer position at which the first reservoir is aligned with said well, a wash position at which wash solution can be introduced into the well, and a second reagent-transfer position at which the second reservoir is aligned with said well, a cover plate attached to the reaction plate such that the transfer plate lies between the reaction plate and the cover plate, means for sealing the well when the well is heated, said sealing means including (a) a sealing pad carried in the transfer plate for traveling in a direction normal to the plane of the transfer plate, and (b) means on the cover plate for biasing the pad against the well, when the transfer plate is moved to a heating position, and means for preventing release of each said reagent from its respective reservoir until that reservoir is aligned with said well.

9. The assembly of claim 8, for use in a DNA probe assay, wherein said analyte ligand includes a nucleic acid with a known target sequence, the solid support is coated with immobilized nucleic acid fragments, said first reagent includes a probe effective to hybridize with both the target sequence and the immobilized fragments, and said second reagent includes a reporter molecule effective to bind, directly or indirectly, to said probe.

10. The assembly of claim 9, wherein said first reagent additionally includes a denaturation agent, and said transfer plate further includes a third reservoir containing an annealing buffer, said third reservoir being alignable with said well to allow transfer of said third reagent to said well.

11. The assembly of claim 10, wherein said transfer plate further includes a fourth reservoir containing a branched nucleic acid fragment effective to bind directly or indirectly to said analyte ligand, and said reporter molecule is effective to bind to the branched fragment.

12. A self-contained assembly for assaying, in a liquid sample, an analyte nucleic acid having a known target sequence, comprising a reaction plate containing a reaction well formed by an elongate, radially extending channel and a solid-phase surface contained in the well and coated with immobilized nucleic acid fragments, a cover plate secured to the reaction plate, and having ports which are alignable with spaced areas of said well, an intermediate transfer plate which includes first, second, third, and fourth reagent reservoirs containing, respectively, (1) a first reagent which includes a denaturation agent and a probe effective to bind to the analyte DNA and to said immobilized fragments, (2) a second reagent which includes an annealing buffer, (3) a third reagent which includes branched nucleic acid fragments effective to bind, directly or indirectly, to said analyte, and (4) a fourth reagent which includes reporter-labeled fragments effective to bind to the branched fragments, where the four reagent reservoirs are designed for sequential addition to said reaction reservoir, said transfer plate further having ports which are alignable with the ports in the cover plate, when the transfer plate is moved to a wash position, providing an enclosed passageway for circulating a solution through said well, means for mounting the transfer plate between the reaction and cover plates for relative rotation with respect thereto, from a home position, at which said first, second, third, and fourth reservoirs are isolated from said well, to first, second, third, and fourth transfer positions at which the first, second, third, and fourth reservoirs are aligned with said well, allowing sequential transfer of the first, second, third, and fourth reagents, respectively, to said well, and means for preventing release of each said reagent from its respective reservoir until that reservoir is aligned with said well.

13. A self-contained assembly for detecting an analyte ligand by detectable, analyte-specific binding to a solid support, comprising a reaction plate defining a well that contains a solid support, said well being capable of holding liquid reagents in contact with the support, said well being formed by an elongate channel, adjacent the reaction plate, a transfer plate containing first and second reagent reservoirs, said transfer plate including wash ports which are alignable with spaced areas in the channel, when the transfer plate is moved to a wash position, forming an enclosed passageway between said reaction plate and said transfer plate for passing a wash solution through the channel, and carried in said first and second reservoirs, first and second reaction reagents, respectively, required for binding of ligand in detectable form to the solid support, means for mounting the transfer plate on the reaction plate for movement thereon to a sample-addition position at which sample can be added to said well, a first reagent-transfer position at which the first reservoir is aligned with said well, a wash position at which said wash ports are aligned with said well so that wash solution can be introduced into the well, and a second reagent-transfer position at which the second reservoir is aligned with said well, and means for preventing release of each said reagent from its respective reservoir until that reservoir is aligned with said well.

* * * * *